United States Patent [19]

Richard et al.

[11] Patent Number: 5,587,151

[45] Date of Patent: Dec. 24, 1996

[54] PHOTOPROTECTIVE/COSMETIC COMPOSITIONS COMPRISING OXANILIDO-SUBSTITUTED POLYORGANOSILOXANES/POLY-ORGANOSILANES

[75] Inventors: Hervé Richard, Villepinte; Madeleine Leduc, Paris; Alain LaGrange, Couvray, all of France

[73] Assignee: L'Oreal, Paris, France

[21] Appl. No.: 560,489

[22] Filed: Nov. 17, 1995

[30] Foreign Application Priority Data

Nov. 17, 1994 [FR] France .................................. 94 13770

[51] Int. Cl.⁶ .............................. A61K 7/42; C08G 77/26
[52] U.S. Cl. ............................... 424/59; 528/26; 556/419
[58] Field of Search ............................... 528/26; 556/419; 424/59

[56] References Cited

U.S. PATENT DOCUMENTS

| | | | |
|---|---|---|---|
| 3,068,153 | 12/1962 | Morehouse | 556/419 |
| 3,683,020 | 8/1972 | Luethi et al. | 260/558 R |
| 3,906,041 | 9/1975 | Hofer et al. | 260/558 S |
| 4,876,299 | 10/1989 | Avar | 524/99 |
| 5,264,604 | 11/1993 | Neri et al. | 556/419 |

FOREIGN PATENT DOCUMENTS 1907403  10/1969  Germany.

*Primary Examiner*—Margaret W. Glass
*Attorney, Agent, or Firm*—Burns, Doane, Swecker & Mathis, L.L.P.

[57] ABSTRACT

Topically applicable sunscreen/cosmetic compositions well suited for enhanced photoprotection of human skin and/or hair against the damaging effects of UV-A and UV-B irradiation, particularly solar radiation, comprise a photoprotecting effective amount of a novel oxanilido-substituted polyorganosiloxane/polyorganosilane having one of the formulae (1) to (3):

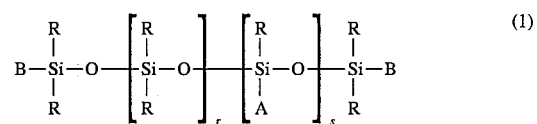

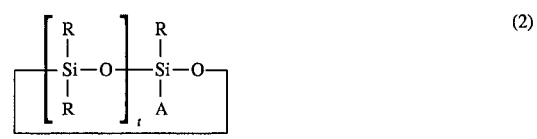

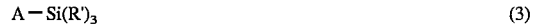

wherein A is a monovalent oxanilide radical which comprises an alkylene or alkyleneoxy bridging group, which is bonded directly to a silicon atom, and which has the formula (4):

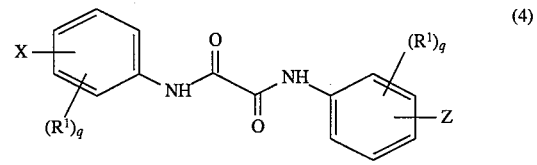

26 Claims, No Drawings

PHOTOPROTECTIVE/COSMETIC COMPOSITIONS COMPRISING OXANILIDO-SUBSTITUTED POLYORGANOSILOXANES/POLY-ORGANOSILANES

CROSS-REFERENCE TO COMPANION APPLICATIONS

Our copending application Ser. No. 08/541,983, filed Oct. 10, 1995, Ser. No. 08/555,334 and Ser. No. 08/555,046, both filed Nov. 8, 1995, and Ser. No. 08/559,941 and Ser. No. 08/559,940, both filed concurrently herewith; each of the above applications is assigned to the assignee hereof.

BACKGROUND OF THE INVENTION

1. Technical Field of the Invention

The present invention relates to novel compounds comprising short-chain, linear or cyclic diorganosiloxanes or triorganosilanes bearing at least one sunscreening oxanilide substituent bonded thereto via an alkylene or alkyleneoxy bridging group.

This invention also relates to novel cosmetic compositions for topical application comprising said oxanilido-substituted polyorganosiloxanes/polyorganosilanes, for the photoprotection of the skin and/or hair against ultraviolet radiation (such compositions hereinafter sometimes simply designated "sunscreen," "sunscreen/cosmetic" or "photoprotective/sunscreen" compositions).

2. Description of the Prior Art

It is known to this art that light radiation of wavelengths of from 280 nm to 400 nm promotes tanning of the human epidermis, and that irradiation of wavelengths of from 280 to 320 nm, i.e, UV-B irradiation, causes erythema and skin burns which can impair the development of a natural tan; hence, such UV-B radiation must thus be screened from the skin.

It is also known to this art that UV-A radiation, of wavelengths of from 320 to 400 nm, which tans the skin, also adversely affects it, in particular in the event of sensitive skin or skin constantly exposed to solar radiation. UV-A irradiation causes, in particular, a loss in the elasticity of the skin and the appearance of wrinkles, promoting a premature aging thereof. Such irradiation promotes triggering of the erythematous reaction or enhances this reaction in certain individuals, and may even be the source of phototoxic or photoallergic reactions. Thus, it is desirable to also screen out UV-A radiation.

A wide variety of compounds intended for the photoprotection (UV-A and/or UV-B) of human skin are known to this art.

Most of these are aromatic compounds displaying an absorption of UV radiation in the region from 280 to 315 nm or in the region of from 315 to 400 nm, or else in both of these regions together. They are, more often than not, formulated in sunscreen compositions as oil-in-water emulsions (namely, a cosmetically acceptable vehicle, carrier or diluent comprising an aqueous continuous dispersing phase and an oily discontinuous dispersed phase) which contain, at various concentrations, one or more traditional lipophilic and/or hydrophilic organic sunscreen compounds comprising an aromatic function suitable for selectively absorbing harmful or deleterious UV radiation. These sunscreen compounds (and the amounts thereof) are selected as a function of the desired specific sun protection factor (the specific protection factor (SPF) being expressed mathematically by the ratio of the irradiation time required to attain the erythemogenic threshold with the UV screening agent to the time required to attain the erythemogenic threshold in the absence of UV screening agent.)

Other than their sunscreen activity, these compounds having anti-UV properties must also display good cosmetic characteristics in the compositions comprised thereof, good solubility in common solvents, and especially fats such as oils and greases, and also good resistance to water and to perspiration (durability). It too is desirable that these sunscreen compositions be nontoxic and do not penetrate into the skin.

Among such prior art aromatic compounds, p-aminobenzoic acid derivatives, benzylidenecamphor derivatives, cinnamon acid derivatives and benzotriazole derivatives are particularly representative. However, certain of these, as well as others of the known sunscreen compounds do not display all of the properties required for an acceptable UV screening agent in sunscreen compositions. In particular, their intrinsic screening activity may be insufficient, ofttimes mandating that relatively large amounts of compound be employed to attain satisfactory screening properties, but at the expense of the cosmetic properties of the ultimate formulations thereof. In addition, their solubility in the different formulations employed for photoprotection is not always sufficiently good (fat solubility in particular), they may not possess sufficient stability to light (photostability) and they may also display poor resistance to water and to sweat.

SUMMARY OF THE INVENTION

Accordingly, a major object of the present invention is the provision of novel oxanilido-substituted silicone/silane sunscreen compounds which display improved properties, and which avoid, or conspicuously ameliorate, the above disadvantages and drawbacks to date characterizing the state of this art.

Thus, it has now unexpectedly been determined that by grafting, in particular via hydrosilylation, one or more specific oxanilide screening derivatives, namely, one or more oxanilide compounds which comprise an alkylene or alkyleneoxy bridging group, to a particular linear or cyclic silicone chain or a particular silane, novel silicone/silane sunscreen compounds are prepared which display, in particular, very high sunscreen activity, both in the UV-A range and in the UV-B range, very good solubility in the common organic solvents and notably in fatty substances such as oils, excellent photostability, and also excellent cosmetic properties, rendering same particularly well suited for formulation into photoprotective/cosmetic compositions for protecting the skin and/or the hair against the damaging or deleterious effects of ultraviolet radiation.

Briefly, the present invention features novel compounds having one of the following formulae (1) to (3):

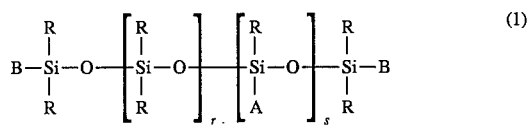
(1)

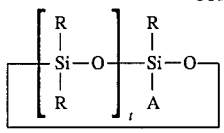 (2)

 (3)

in which the radicals R, which may be identical or different, are each a $C_1$–$C_{10}$ alkyl, phenyl or 3,3,3-trifluoropropyl radical, at least 80% by number of the radicals R being methyl radicals; the radicals B, which may be identical or different, are each a radical R or a radical A as defined below; the radicals R', which may be identical or different, are each a $C_1$–$C_8$ alkyl radical or a phenyl radical; r is an integer ranging from 0 to 50, inclusive, and s is an integer equal to 0 or 1, with the proviso that, if s is zero, then at least one of the two radicals B is a radical A; t is an integer ranging from 2 to 10, inclusive; and the radical A is a monovalent radical bonded directly to a silicon atom and which has the following formula (4):

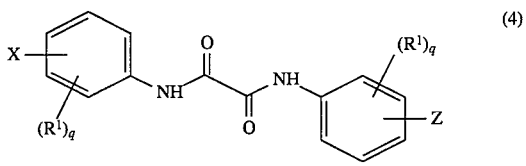 (4)

wherein X is a divalent radical —Y— having the following formula (5):

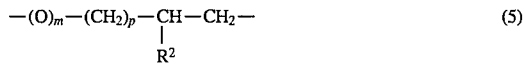 (5)

in which $R^2$ is a hydrogen atom or a $C_1$–$C_4$ alkyl radical; p is an integer ranging from 0 to 10, inclusive; m is 0 or 1; the —$CH_2$— endgroup is directly bonded to a silicon atom; Z is a hydrogen atom or a divalent radical —Y—; q is an integer ranging from 0 to 3 inclusive; and the radicals $R^1$, which may be identical or different, are each a $C_1$–$C_8$ alkyl radical or $C_1$–$C_6$ alkoxy radical, with the proviso that, when the radicals $R^1$ are alkoxy radicals, two adjacent radicals $R^1$ (q≧2) may together form an alkylidenedioxy group in which the alkylidene moiety contains 1 or 2 carbon atoms.

DETAILED DESCRIPTION OF BEST MODE AND PREFERRED EMBODIMENTS OF THE INVENTION

More particularly according to the present invention, in the above formulae (1) to (3), A is thus the radical derived from the oxanilide which, after bonding to the starting short silicone chain or to the starting silane, imparts absorbing properties to the compounds of linear diorganosiloxane type (formula (1)), or of cyclic diorganosiloxane type (formula (2)), or of triorganosilane type (formula (3)), with respect to ultraviolet radiation within a wavelength region which may range from 280 to 400 nm. As indicated above, and as is apparent from the definition of the above formula (4), this group necessarily comprises at least one alkylene or alkyleneoxy function defining a bridging structural unit which ensures grafting of the oxanilide to the silicone backbone or to the silane. One of the advantages of the compounds according to the invention is that, depending on the nature and/or position of the various substituents borne by the screening nucleus A, either purely UV-A screening agents or, to the contrary, purely UV-B screening agents, are provided, exhibiting particularly high extinction coefficients.

Also as is apparent from the above formula (4), linking radical —(O)$_m$—(CH$_2$)$_p$—CH(R$^2$)—CH$_2$— (i.e., a divalent radical —Y— of formula (5)) may, according to the present invention, be grafted onto the structural unit derived from the oxanilide, which thus ensures bonding of said structural unit to a silicon atom of the silicone backbone or of the silane, at any one of the available positions capable of being occupied by the radicals X or Z on the two aromatic rings of the oxanilide, the —(O)$_m$— endgroup of said bridging moiety becoming bonded to the structural unit derived from the oxanilide and its —CH$_2$— endgroup becoming bonded to a silicon atom of the silicone backbone or of the silane. It should appreciated that the screening moiety derived from the oxanilide may thus have either a single bridging structural unit (in the event that Z is hydrogen) or, to the contrary, two bridging structural units (in the event that Z is also a divalent radical —Y—) and may thus be joined to two different silicone backbones, or nuclei, or to two different silyl structural units.

According to the present invention, the radical X is preferably in the ortho- or para position on the aromatic ring from which it depends.

Likewise, in the event that Z is a second bridging structural unit —Y—, this unit is preferably in the ortho- or para-position on the aromatic ring member from which it depends.

In the above formulae (1) to (3), the alkyl radicals can be linear or branched and are advantageously selected from among methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The preferred alkyl radicals R, R' and B according to the invention are methyl, ethyl, propyl, n-butyl, n-octyl and 2-ethylhexyl radicals. Even more preferably, the radicals R, R' and B are all methyl radicals. As regards the alkoxy radicals, these are advantageously selected from among methoxy, ethoxy, n-propoxy, isopropoxy, n-butoxy and isobutoxy radicals.

Among the compounds of the above formulae (1) to (3), preferred are those corresponding to formula (1) or to formula (2), namely, linear or cyclic short-chain diorganosiloxanes.

Among the linear or cyclic diorganosiloxanes according to the present invention, preferred are the random derivatives or well-defined block derivatives having at least one, and even more preferably all, of the following characteristics and definitions:

R is alkyl and, even more preferably, is methyl,

B is alkyl and, even more preferably, is methyl (in the case of the linear compounds of formula (1)), r ranges from 0 to 3, inclusive (in the case of the linear compounds of formula (1)), t ranges from 2 to 4, inclusive (in the case of the cyclic compounds of formula (2)), q is zero or equal to 1, $R^1$ is H (q=0) or methoxy (q≠0), p is zero or equal to 1, $R^2$ is H or methyl.

To prepare the silicone sunscreen agents of formulae (1) and (2), a standard hydrosilylation reaction is employed, i.e.:

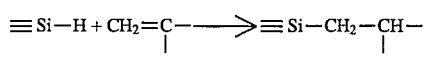

starting from the corresponding silicone in which, for example, all of the radicals A are hydrogen atoms. This starting silicone will hereinafter be designated the derivative containing SiH; the SiH groups may be present in the silicone backbone and/or at the ends of the silicone chain. These derivatives containing SiH are well known compounds in the silicone industry and are widely available commercially. They are described, for example, in U.S. Pat. Nos. 3,220,972, 3,697,473 and 4,340,709.

This derivative containing SiH may thus be represented, depending on the particular case, either by the following formula (1a):

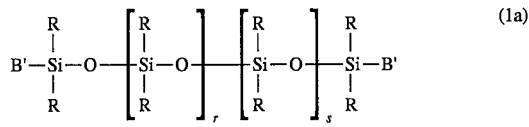

in which R, r and s are as defined above in respect of the formula (1) and the radicals B', which may be identical or different, are selected from among the radicals R and a hydrogen atom, with the proviso that, if s=0, then one, and only one, of the radicals B' must be a hydrogen atom, or by the following formula (2a):

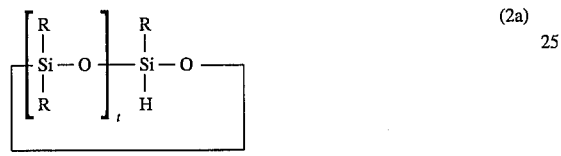

in which R and t are as defined above in respect of the formula (2).

A conventional hydrosilylation reaction is thus carried out on this SiH-containing derivative of formula (1a) or (2a), which reaction is conducted in the presence of a catalytically effective amount of a platinum catalyst, with an organic oxanilide compound having the following formula (4a):

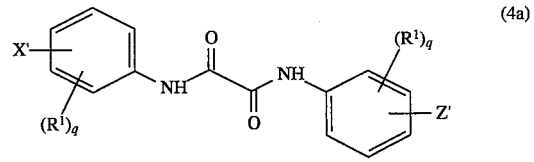

in which $R^1$ and q are as defined above for formula (4), and X', instead of representing the divalent radical —Y— of formula (5) defined above, is, in this event, the corresponding unsaturated homologous monovalent radical —Y' having the formula (5a):

in which $R^2$, m and p are as defined above in respect of the formula (5), and Z' is a monoradical —Y' as defined above.

Exemplary compounds of formula (4a) according to the present invention include, in particular:

(a) N,N'-Bis[4-(2-methylallyloxy)phenyl]oxalamide;
(b) N,N'-Bis[2-(2-methylallyloxy)phenyl]oxalamide;
(c) N,N'-Bis(2-allyloxy-5-methoxyphenyl)oxalamide.

Suitable processes for the preparation of the compounds of formula (4a) above are described in FR-B-1,506,632 and FR-B-1,516,276. According to these patents, the subject compounds may thus be prepared via known techniques, as follows:

(1) For the symmetric derivatives: by reacting, in a first stage, oxalic acid or esters thereof with appropriate aromatic amines, according to the following reaction scheme (6):

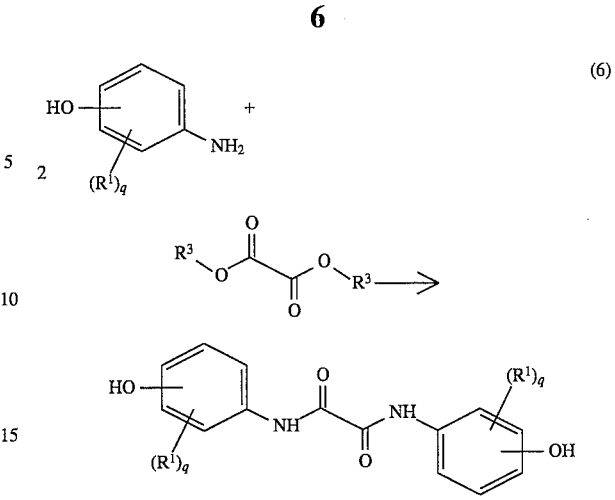

in which $R^1$ and q are as defined above in respect of formula (4), and $R^3$ is a hydrogen atom or a methyl or ethyl radical.

Then, in a second stage, the compounds thus obtained may subsequently be alkylated with halides of the following formula (7):

in which $R^2$ and p are as defined above in respect of formula (5) and Hal is a halogen atom selected from between chlorine and bromine, by means of which the desired derivatives of formula (4a), in which Z' represents —Y', are ultimately prepared.

(2) For the asymmetric derivatives: the reaction for preparing the derivatives described in scheme (6) is carried out in two stages: (i) reacting dimethyl or diethyl oxalate with one equivalent of an aromatic amine substituted by a hydroxyl substituent, followed by (ii) reacting the compound obtained in (i) with a second equivalent of an amine not containing hydroxyl substituents. The reaction product obtained in (ii) is then alkylated with halides of the above formula (7) by means of which the desired compounds of formula (4a), in which Z'=H, are ultimately prepared.

(3) The derivatives of formula (4a) in which the m in formula (5a) is equal to 0 may be prepared from the corresponding compounds of formula (4a) in which m=1, via Claisen rearrangement followed by an alkylation of the free hydroxyl group with a $C_1$–$C_8$ alkyl halide.

The platinum catalysts used to carry out the hydrosilylation reaction between the compounds of formula (1a) or (2a) above and the compound of formula (4a) above are well-known and widely described in the literature. Exemplary thereof are, in particular, the complexes of platinum and an organic compound described in U.S. Pat. Nos. 3,159,601, 3,159,602 and 3,220,972 and European Patent Applications EP-A-0,057,459, EP-A-0,188,978 and EP-A-0,190,530 and the complexes of platinum and vinyl organopolysiloxanes described in U.S. Pat. Nos. 3,419,593, 3,377,432 and 3,814,730. To react the compounds of formula (1a) or (2a) with the compound of formulae (4a), an amount of platinum catalyst, calculated as weight of platinum metal, ranging from 5 to 600 ppm, preferably from 10 to 200 ppm, based on the weight of compounds of formula (1a) or (2a), is generally employed. The hydrosilylation reaction may be carried out in bulk or in a volatile organic solvent such as toluene, heptane, xylene, tetrahydrofuran or tetrachloroethylene. It is generally desirable to heat the reaction mixture to a temperature ranging from 60° to 120° C. for the period of time required for the reaction to be driven to completion. The compound of formula (1a) or (2a) may be added dropwise to the compound of formula (4a) in solution in an organic solvent containing the catalyst. The compound of formula (1a) or (2a) and the compound of formula (4a) may also be added simultaneously to a suspension of catalyst in an organic solvent. It is preferred to monitor that the reaction is complete by assaying the residual SiH using alcoholic potassium hydroxide, followed by removal of the solvent, for example by distillation under reduced pressure. The crude oil obtained may be purified, for example by cascading same through an absorbent column of silica.

As regards the preparation of the screening agents of triorganosilane type of formula (3) given above, the process may be carried out as indicated above, again by a hydrosilylation reaction, between a starting silane of formula (R'($_3$SiH (formula (3a), in which R' has the same definition as for the compound of formula (3)), and an organic oxanilide derivative of formula (4a) defined above.

Also as indicated above, the compounds of formulae (1) to (3) above exhibit excellent intrinsic screening activity with respect to UV-A and UV-B ultraviolet radiation, depending upon the particular chemical structure thereof. By admixing compounds of different structure, namely, more specifically, by mixing compounds according to the invention displaying purely UV-A activity with products according to the invention displaying purely UV-B activity, it is thus possible to provide a composition which will display overall an exceptional sunscreen activity over the entire range of harmful UV (UV-A+UV-B), which is a considerable advantage. In addition, taking account of their highly liposoluble nature, the compounds of formulae (1) to (3) may be used in high concentrations, thereby imparting very high specific protection factors to the final compositions; moreover, they distribute themselves uniformly in standard cosmetic vehicles comprising at least one fatty phase or at least one cosmetically acceptable organic solvent, and may thus be applied to the skin or hair to form an effective protective film. Too, their cosmetic properties are very good, namely, in particular, compared with the silicone screening agents of the prior art, these products are less sticky and render the skin or hair softer.

Thus, the present invention also features cosmetic compositions comprising, in a cosmetically acceptable vehicle, carrier or diluent, preferably including at least one fatty phase or at least one organic solvent, an effective photoprotective amount of at least one compound of the above formulae (1) to (3).

The compounds of formulae (1) to (3) are advantageously present in proportions ranging from 0.1% to 20% by weight, and preferably from 0.5% to 10% by weight, relative to the total weight of the composition.

The cosmetic compositions of the invention may be used as compositions for protecting the human epidermis or hair against ultraviolet rays, as sunscreen compositions or as makeup products.

These compositions may, in particular, be in the form of a lotion, a thickened lotion, a gel, a cream, an ointment, a milk, a powder or a solid stick and may optionally be packaged as an aerosol, as a foam, a mousse or a spray.

They can contain the usual cosmetic adjuvants and additives, such as fats and fatty substances, organic solvents, silicones, thickeners, softeners, emollients, complementary sunscreens, anti-foaming agents, moisturizing or hydrating agents, fragrances and perfumes, preservatives, surfactants, fillers, sequestering agents, anionic, cationic, nonionic or amphoteric polymers or mixtures thereof, propellants, basifying or acidifying agents, colorants, dyes, pigments or nanopigments, in particular those designed to provide a complementary photoprotective effect by physically blocking out ultraviolet radiation, or any other ingredient customarily used in cosmetics, especially for the production of sunscreen compositions.

Exemplary of the organic solvents are the lower alcohols and polyols, such as ethanol, isopropanol, propylene glycol, glycerol and sorbitol.

The fats or fatty substances can comprise of an oil or wax or mixtures thereof, fatty acids, fatty acid esters, fatty alcohols, petrolatum, paraffin, lanolin, hydrogenated lanolin or acetylated lanolin. The oils may be selected from among animal, vegetable, mineral or synthetic oils and, in particular, hydrogenated palm oil, hydrogenated castor oil, liquid petrolatum, liquid paraffin, purcellin oil, volatile or non-volatile silicone oils, and isoparaffins.

When the cosmetic composition according to the invention are used for protecting the human epidermis against the deleterious or damaging effects of UV irradiation or as sunscreen compositions, they are advantageously formulated as a suspension or dispersion in solvents or fatty substances, or, alternatively, in the form of an emulsion (in particular of O/W or W/O type, but preferably of O/W type) such as a cream or a milk, or of a vesicle dispersion, or as an ointment, a salve, a gel, a solid stick or an aerosol foam. The emulsions may additionally contain anionic, nonionic, cationic or amphoteric surface-active agents.

When the cosmetic compositions according to the invention are used for the photoprotection of the hair, they can be formulated as a shampoo, a lotion, a gel or rinse, to be applied before or after shampooing, before or after dyeing or bleaching, before, during or after permanent-waving or straightening of the hair, or as a styling or treatment lotion or gel, a blow-drying or hair-setting lotion or gel, a hair lacquer, a permanent-waving or hair-straightening composition, or a composition for dyeing or bleaching the hair.

When the cosmetic compositions according to the invention are used as makeup products for the eyelashes, the eyebrows, the skin or the hair, such as a skin-treatment cream, a foundation, a lipstick, an eye shadow, a blush, an eyeliner, a mascara or a coloring gel, they can be formulated in solid or pasty, anhydrous or aqueous form, such as oil-in-water or water-in-oil emulsions, suspensions or gels.

The cosmetic treatment of the skin or hair to protect same against the deleterious effects of ultraviolet radiation, in particular solar radiation, comprising topically applying to the skin or hair an effective amount of a sunscreen/cosmetic composition as described above, or of a compound of the above formulae (1) to (3).

In order to further illustrate the present invention and the advantages thereof, the following specific examples are given, it being understood that same are intended only as illustrative and in nowise limitative.

EXAMPLE 1

This example relates to the preparation of N,N'-bis{4-[3-[1,3,3,3-tetramethyl-1-[(trimethylsilyl)oxy]disiloxanyl]-2-methylpropyloxy]phenyl}oxalamide, namely, a compound in accordance with the present invention, having the structural formula:

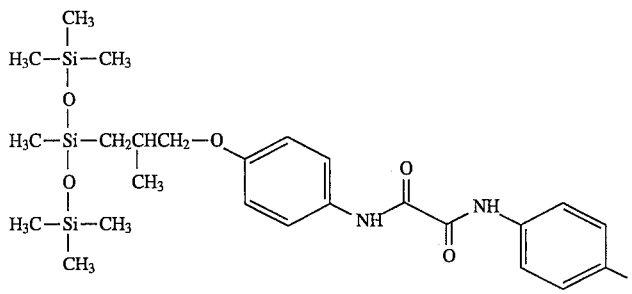

(this compound has formula (1) in which R=B=methyl; r=0, s=1; q=0; X=Z=—Y— (in the para position) with, for Y: m=p=1 and $R^2$=methyl).

(a) First stage:

para-Aminophenol (109 g; 1 mol), dimethyl oxalate (59 g; 0.5 mol) and 500 ml of ortho-dichlorobenzene were introduced into a fully-equipped round-bottomed flask. The mixture was heated at 140° C. for 4 hours, the methanol formed was distilled off and heating was continued for one hour at 170° C. After cooling, the reaction mixture was filtered; the blue paste thus obtained was washed with toluene, then with ethanol, and dried under vacuum. 61 g (yield: 44 %) of N,N'-bis(4-hydroxyphenyl)oxalamide, having the following characteristics, were thus obtained:

Purple-grey powder m.p.: >250° C.

(b) Second stage:

27.2 g of the compound obtained above, 200 ml of dry DMSO and 28 g of potassium carbonate were introduced into a fully-equipped round-bottomed flask. The mixture was heated to 65° C., under nitrogen. Methallyl chloride (20 g; 0.22 mol) was added dropwise thereto over 20 minutes. The mixture was maintained under stirring at 65° C. for 6 hours, under nitrogen. It was cooled and 200 ml of methanol were added. The solid obtained was filtered off, washed with methanol and recrystallized from 400 ml of DMF. 14.3 g of N,N'-bis[4-(2-methylallyloxy)phenyl]oxalamide, having the following characteristics, were thus recovered:

White powder

M.p.: 239°–240° C.

(c) Third stage:

7.6 g (i.e., 0.02 mol) of the compound obtained above and 16 ml of toluene were introduced into a fully-equipped round-bottomed flask. The mixture was heated to 80° C., under nitrogen. The hydrosilylation catalyst (complex containing 3–3.5% of Pt in cyclovinylmethylsiloxane, marketed by Hüls under the trademark Petrarch PC085: 100 µl) was then added, followed by 9.79 g of heptamethyltrisiloxane. After 6 hours at 80° C. under nitrogen, the reaction medium was concentrated and chromatographed on silica under pressure (eluent: $CH_2Cl_2$/heptane 60/40). 16.5 g (yield: 78%) of the desired final compound, having the following characteristics, were thus recovered:

White powder m.p.: 84°–86° C.

Elemental analysis: theoretical: C 52.38, H 8.30, N 3.39, Si 20.41; found: C 52.58, H 8.34, N 3.37, Si 19.93.

The UV absorption characteristics (measured in ethanol) of this compound were as follows: $\lambda_{max}$=293 nm, $\epsilon_{max}$=23,000.

This compound is thus a very effective sunscreen which is active in the UV-B range.

EXAMPLE 2

This example relates to the preparation of N,N'-bis{2-[3-[1,3,3,3-tetramethyl-1-[(trimethylsilyl)oxy]disiloxanyl]-2-methylpropyloxy]phenyl}oxalamide, namely, of another compound in accordance with the present invention, having the formula:

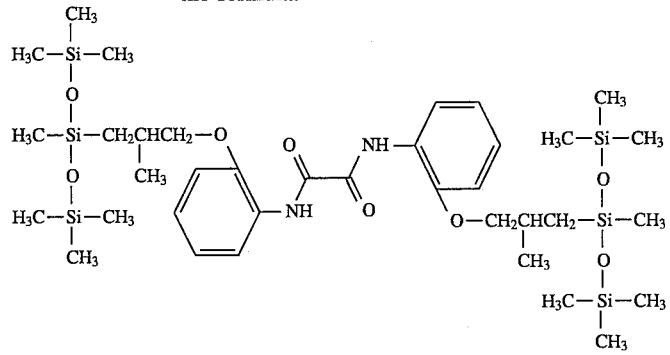

(this compound has formula (1) in which R=B=methyl; r=0, s=1; q=0; X=Z=—Y— (in the para position) with, for Y: m=p=1 and $R^2$=methyl).

(a) First stage:

ortho-Aminophenol (65.5 g; 0.6 mol), dimethyl oxalate (35.4 g; 0.3 mol) and 300 ml of 1,2-dichlorobenzene were introduced into a fully-equipped round-bottomed flask. The mixture was heated at 140° C. for 4 hours, the methanol formed was distilled off and heating was continued for one hour at 170° C. After cooling, the reaction mixture was filtered. The solid obtained was washed with ethanol. 69.8 g (yield: 85%) of N,N'-bis(2-hydroxyphenyl)oxalamide, having the following characteristics, were thus recovered:

Light beige powder
m.p.: >250° C.

(b) Second stage:

59.8 g of the compound obtained above, 440 ml of dry DMSO and 61.6 g of potassium carbonate were introduced into a fully-equipped round-bottomed flask. The mixture was then heated to 65° C., under nitrogen. Methallyl chloride (43.8 g; 0.484 mol) was then added dropwise thereto over 30 minutes. The mixture was then maintained under stirring at 65° C. for 4 hours, under nitrogen. It was cooled and 200 ml of methanol were added. The solid obtained was filtered off, washed with methanol, with water and then again with methanol. 77.4 g of N,N'-bis[2-(2-methylallyloxy)phenyl]oxalamide, having the following characteristics, were thus obtained:

Slightly beige powder
m.p.: 184° C.

(c) Third stage:

19 g (i.e., 0.05 mol) of the compound obtained above and 30 ml of toluene were introduced into a fully-equipped round-bottomed flask. The mixture was heated to 80° C., under nitrogen. The hydrosilylation catalyst (complex containing 3–3.5% of Pt in cyclovinylmethylsiloxane, marketed by Hüls under the trademark Petrarch PC085: 100 μl) was then added, followed by 24.5 g of heptamethyltrisiloxane. After 3 hours at reflux under nitrogen, the reaction medium was concentrated. After recrystallization from methanol, 28 g (yield: 68%) of the desired final compound, having the following characteristics, were recovered:

White powder
m.p.: 77° C.

Elemental analysis: theoretical: C 52.38, H 8.30, N 3.39, Si 20.41; found: C 52.36, H 8.27, N 3.56, Si 20.15.

The UV absorption characteristics (measured in ethanol) of this compound were as follows: $\lambda_{max}$=307 nm, $\lambda_{max}$=18, 425.

This compound is thus a very effective sunscreen which is active in the UV-B range.

EXAMPLE 3

A photoprotective/sunscreen formulation in accordance with the invention was prepared in the form of an oil-in-water sunscreen cream containing:

| | |
|---|---|
| (a) Compound of Example 1 | 3 g |
| (b) Mixture of cetylstearyl alcohol and cetylstearyl alcohol oxyethylenated with 33 mol of EO ("DEHSCONET 390" marketed by Tensia) | 8 g |
| (c) Mixture of glyceryl mono- and distearate which was not self-emulsifiable | 1.5 g |
| (d) Cetyl alcohol | 1.5 g |
| (e) $C_{12}$–$C_{15}$ alkyl benzoate ("FINSOLV TN" marketed by Finetex) | 12 g |
| (f) Polydimethylsiloxane ("SILBIONE OIL 70 047 V 300" marketed by Rhône-Poulenc) | 1 g |

-continued

| | | |
|---|---|---|
| (g) 2-Ethylhexyl p-methoxycinnamate (complementary sunscreen marketed under the trademark "PARSOL MCX" by Givaudan-Roure) | | 5 g |
| (h) Nanopigment-grade titanium dioxide ("MT 100 T" marketed by Tayca) | | 1 g |
| (i) Glycerol | | 15 g |
| (j) Benzene-1,4-di(3-methylidene-10-camphosulfonic) acid (complementary sunscreen described in FR-2,528,420) | | 6.06 g |
| (k) Triethanolamine | | 1.2 g |
| (l) Fragrance, preservative | qs | |
| (m) Water | qs | 100 g |

This cream was formulated according to the standard techniques for the preparation of emulsions, by dissolving the liposoluble screening agents in the fatty phase containing the emulsifying agents, heating this fatty phase to about 70°–80° C. and adding, with vigorous stirring, the water which had been heated to the same temperature. Stirring was maintained for 10 to 15 minutes and, after permitting this formulation to cool with moderate stirring, the fragrance and preservative were then finally added at about 40° C.

EXAMPLE 4

Another specific example of a photoprotective/sunscreen cosmetic composition was prepared in accordance with the invention, namely, an oil-in-water sunscreen milk containing:

| | | |
|---|---|---|
| (a) Compound of Example 1 | | 2 g |
| (b) Mixture of cetylstearyl alcohol and cetylstrearyl alcohol oxyethylenated with 33 mol of EO ("DEHSCONET 390" marketed by Tensia) | | 3 g |
| (c) Mixture of glyceryl mono- and distearate which is not self-emulsifiable | | 1 g |
| (d) Cetyl alcohol | | 1 g |
| (e) $C_{12}$–$C_{15}$ alkyl benzoate ("FINSOLV TN" marketed by Finetex) | | 9 g |
| (f) Polydimethylsiloxane ("SILBIONE OIL 70 047 V 300" marketed by Rhône-Poulenc) | | 1 g |
| (g) 2-Ethylhexyl 2-cyano-3,3-diphenylacrylate (complementary sunscreen marketed under the trademark "UNINUL N 539" by BASF) | | 6 g |
| (h) 4-tert-Butyl-4'-methoxydibenzoylmethane (complementary sunscreen marketed under the trademark "PARSOL 1789" by Givaudan-Roure) | | 2 g |
| (i) Glycerol | | 2 g |
| (j) Fragrance, preservative | qs | |
| (k) Water | qs | 100 g |

This cream was formulated according to the standard techniques for the preparation of emulsions, by dissolving the liposoluble screening agents in the fatty phase containing the emulsifying agents, heating this fatty phase to about 70°–80° C. and adding, with vigorous stirring, the water which had been heated to the same temperature. Stirring was maintained for 10 to 15 minutes and, after permitting the composition to cool with moderate stirring, the fragrance and preservative were lastly added at about 40° C.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. An oxanilido-substituted polyorganosiloxane/polyorganosilane compound having one of the formulae (1) to (3):

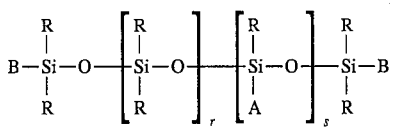

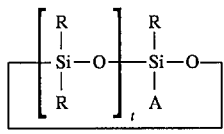

in which the radicals R, which may be identical or different, are each a $C_1-C_{10}$ alkyl, phenyl or 3,3,3-trifluoropropyl radical, at least 80% by number of the radicals R being methyl radicals; the radicals B, which may be identical or different, are each a radical R or a radical A as defined below; the radicals R', which may be identical or different, are each a $C_1-C_8$ alkyl radical or a phenyl radical; r is an integer ranging from 0 to 50, inclusive, and s is an integer equal to 0 or 1, with the proviso that, if s is zero, then at least one of the two radicals B is a radical A; t is an integer ranging from 2 to 10, inclusive; and the radical A is a monovalent radical bonded directly to a silicon atom and which has the following formula (4):

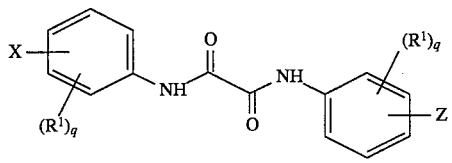

wherein X is a divalent radical —Y— having the following formula (5):

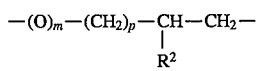

in which $R^2$ is a hydrogen atom or a $C_1-C_4$ alkyl radical; p is an integer ranging from 0 to 10, inclusive; m is 0 or 1; the —$CH_2$— endgroup is directly bonded to a silicon atom; Z is a hydrogen atom or a divalent radical —Y—; q is an integer ranging from 0 to 3 inclusive; and the radicals $R^1$, which may be identical or different, are each a $C_1-C_8$ alkyl radical or $C_1-C_6$ alkoxy radical, with the proviso that, when the radicals $R^1$ are alkoxy radicals, two adjacent radicals $R^1$ ($q \geq 2$) may together form an alkylidenedioxy group in which the alkylidene moiety contains 1 or 2 carbon atoms.

2. A polyorganosiloxane/polyorganosilane compound as defined by claim 1, having the formula (1).

3. A polyorganosiloxane/polyorganosilane compound as defined by claim 1, having the formula (2).

4. A polyorganosiloxane/polyorganosilane compound as defined by claim 1, having the formula (3).

5. A polyorganosiloxane/polyorganosilane compound as defined by claims 2 or 3, wherein the formulae (1) and (2), the radicals R are alkyl radicals.

6. A polyorganosiloxane/polyorganosilane compound as defined by claim 5, said radicals R being methyl, ethyl, propyl, n-butyl, n-octyl or 2-ethylhexyl radicals.

7. A polyorganosiloxane/polyorganosilane compound as defined by claim 6, said radicals R being methyl radicals.

8. A polyorganosiloxane/polyorganosilane compound as defined by claim 2, wherein formula (1), the radicals B are alkyl radicals.

9. A polyorganosiloxane/polyorganosilane compound as defined by claim 8, said radicals B being methyl, ethyl, propyl, n-butyl, n-octyl or 2-ethylhexyl radicals.

10. A polyorganosiloxane/polyorganosilane compound as defined by claim 9, said radicals B being methyl radicals.

11. A polyorganosiloxane/polyorganosilane compound as defined by claim 2, wherein formula (1), r ranges from 0 to 3.

12. A polyorganosiloxane/polyorganosilane compound as defined by claim 3, wherein formula (2), t ranges from 2 to 4.

13. A polyorganosiloxane/polyorganosilane compound as defined by claim 4, wherein formula (3), the radicals R' are methyl, ethyl, propyl, n-butyl, n-octyl or 2-ethylhexyl radicals.

14. A polyorganosiloxane/polyorganosilane compound as defined by claim 13, said radicals R' being methyl radicals.

15. A polyorganosiloxane/polyorganosilane compound as defined by claim 1, wherein the formulae (1) to (3), q is other than zero and the radicals $R^1$ are alkoxy radicals.

16. A polyorganosiloxane/polyorganosilane compound as defined by claim 1, wherein the formulae (1) to (3), q is zero.

17. A polyorganosiloxane/polyorganosilane compound as defined by claim 1, wherein formula (5), p is zero or 1.

18. A polyorganosiloxane/polyorganosilane compound as defined by claim 1, wherein formula (5), $R^2$ is hydrogen or a methyl radical.

19. A polyorganosiloxane/polyorganosilane compound as defined by claim 1, wherein formula (4), the radical X is in the ortho- or para-position on the aromatic ring member from which it depends.

20. A polyorganosiloxane/polyorganosilane compound as defined by claim 1, wherein formula (4), the radical Z is —Y— and is in the ortho- or para-position on the aromatic ring member from which it depends.

21. A topically applicable sunscreen/cosmetic composition adopted for the photoprotection of human skin and/or hair, comprising a photoprotecting effective amount of a polyorganosiloxane/polyorganosilane compound as defined by claim 1, in a cosmetically acceptable vehicle, carrier or diluent therefor.

22. The sunscreen/cosmetic composition as defined by claim 21, said cosmetically acceptable vehicle, carrier or diluent comprising at least one fatty phase or at least one organic solvent.

23. The sunscreen/cosmetic composition as defined by claim 21, comprising an oil-in-water or water-in-oil emulsion.

24. The sunscreen/cosmetic composition as defined by claim 21, comprising from 0.1% to 20% by weight of said photoprotecting compound.

25. A method for protecting human skin and/or hair against the deleterious effects of ultraviolet irradiation, comprising topically applying thereto an effective amount of the sunscreen/cosmetic composition as defined by claim 21.

26. A method for protecting human skin and/or hair against the deleterious effects of solar radiation, comprising topically applying thereto an effective amount of the sunscreen/cosmetic composition as defined by claim 21.

* * * * *